United States Patent [19]

Truog et al.

[11] Patent Number: 6,114,161
[45] Date of Patent: Sep. 5, 2000

[54] ANTITUMOR PREPARATIONS

[75] Inventors: Peter Truog, Basel; Peter Rothlisberger, Zurich, both of Switzerland

[73] Assignee: Lunamed AG, Bottmingen, Switzerland

[21] Appl. No.: 08/875,018

[22] PCT Filed: Jan. 24, 1996

[86] PCT No.: PCT/EP96/00309

§ 371 Date: Oct. 28, 1997

§ 102(e) Date: Oct. 28, 1997

[87] PCT Pub. No.: WO96/23896

PCT Pub. Date: Aug. 8, 1996

[30] Foreign Application Priority Data

Jan. 30, 1995 [EP] European Pat. Off. .............. 95101208

[51] Int. Cl.$^7$ .............................. C12N 1/00; C12N 1/04; C12N 1/12; C12N 1/20
[52] U.S. Cl. ..................... 435/243; 435/247; 435/248; 435/252.1; 435/253.4; 435/260; 435/885
[58] Field of Search .................. 435/253.4, 248, 435/252.1, 260, 243, 247, 885

[56] References Cited

U.S. PATENT DOCUMENTS 5,610,011  3/1997  Smith et al. .

*Primary Examiner*—Anthony C. Caputa
*Assistant Examiner*—John K. Weatherspoon
*Attorney, Agent, or Firm*—Mathews, Collins, Shepherd & Gould, P.A.

[57] ABSTRACT

A new bacteria species within the genus Streptococcus is disclosed, designated as Streptococcus sp PT DSM 8747. From this bacteria species a lipoteichoic acid LTA can be isolated which has a lipid anchor, galacto-furanosyl-beta-1-3-glycerol with different rests of fatty acids esterified to the two adjacent hydroxy groups in the glycerol moiety and a non-glycosylated, linear, unbranched GroP chain. The hydrophilic backbone may comprise 10 glycerophosphate units esterified with D-alanine in an extent of about 30%. The invention further concerns a pharmaceutical composition with the LTA, optionally together with a monokine and/or hyaluronidase, a method of treating cancer comprising administrating an antitumor effective amount thereof, a method of producing the LTA, and degradation products of the LTA and their use.

3 Claims, 1 Drawing Sheet

ANTITUMOR PREPARATIONS

RELATED APPLICATIONS

Applicant claims priority based on European patent application no. 95101208.7, filed Jan. 30, 1995, for the United Kingdom, and international application no. PCT/EP96/00309, filed Jan. 24, 1996.

FIELD OF THE INVENTION

The invention concerns a new lipoteichoic acid (in the following LTA-T), a pharmaceutical composition comprising it, optionally together with a monokine and/or hyaluronidase, a method of treating cancer comprising administration of an antitumor effective amount thereof, a method of producing the new compound and the new pharmaceutical composition, two degradation products of the new LTA-T and their use, and the new Streptococcus strain from which the new compound can be isolated.

BACKGROUND OF THE INVENTION

Lipoteichoic acids (LTAs) are a group of amphipathic substances found in the cell wall of gram-positive bacteria extending from the outer cell membrane through the cell wall to the surface. The main group of LTAs consists of a hydrophilic poly(glycerophosphate) backbone and a hydrophobic glycolipid moiety. The hydrophilic backbone may be substituted with alanine, hexoses and hexosamines. The glycolipids de-scribed so far were mainly dihexosylglycerols and some trihexosylglycerols. Lipoteichoic acids show genus and species variation in the degree of polymerization of the hydrophilic chain, in the nature and degree of glycosidic substitution, in the extent of D-alanyl ester substitution, and in the structure of the lipid moiety (A. J. Wicken et al., Science, 187, 1161–1167, (1975), and Microbiology, 360–365, (1977); Fischer W., Physiology of lipoteichoic acids in bacteria. Adv. Microb. Physiol., 29(233): 233–302 (1988), Fischer W., Mannsfeld T., Hagen G., On the basic structure of poly-(glycerophosphate) lipoteichoic acids, Biochem. Cell Biol., 68(1): 33–43, (1990).

LTAs have been reported as having antitumor activity (EP 135 820; U.S. Pat. No. 4,678,773; A. Yamamoto et. al. 1985, Br. J. Cancer, 51, 739–742; and H. Usami et. al., Br. J. Cancer, 1988, 57, 70–73).

LTAs were isolated from e. g. *Lactobacillus helveticus* (NCIB 8025), *Lactobacillus fermenti* (NCTC 6991), *Streptococcus faecalis*, 39, *Streptococcus lactis* (ATCC 9936), *Streptococcus mutans*, AHT (A. J. Wicken et al, 1975), and *Streptococcus pyogenes* SV strain (ATCC 21059) (EP 135 820, U.S. Pat. No. 4,678,773, H. Usami et. al. 1985).

A glycerophosphogalactofuranosylglycerol has been described by J. H. Veerkamp and F. W. van Schalk, (1974), Biochim et Biophys. Acta, 348, pages 370–387. The isolation from *Bifidobacterium bifidum* var. *pennsylvanicus*, however did not result in pure compounds. An amount of 10 to 20% of the corresponding galactopyranosyl compounds was still present. The structure of the major compounds from this bacterium was later proposed by Werner Fischer, Eur. J. Biochem, 165, 639–646 (1987). It is unrelated to the LTAs of the present invention.

K. K:Brown disclose in WO 94/20115 the use of hyaluronic acid for the treatment of cancer whereby also lipoteichoic acids may be used in combination therewith.

A streptococcal acid glycoprotein (SAGP) with antitumor activity was isolated by M. Kanaoka et. al., Jp. J. Cancer Res. (Gann), 78, 1409–1414, (1987) from the low virulent strain *Streptococcus pyogenes* Su ATCC 21060. OK-432, a cell preparation from said strain, has found clinically use as an antitumor agent. However, in the meantime it was withdrawn from the market.

The LTAs described up to now carried more than one monosaccharide in the glycceroglycolipid anchor. Different glycolipid structures have been described by Fischer et al. 1988 and 1990.

An LTA with a monohexosyldiacylglyceroglycolipid as lipid anchor has not been described so far.

OBJECT OF THE INVENTION

It is an object of the invention to provide a purified new LTA with a strong antitumor activity.

It is a further object to provide pharmaceutical preparations comprising this new LTA, optionally in combination with a monokine and/or hyaluronidase.

It is a further object to provide a method of treating cancer comprising administration of an antitumor effective amount of the new LTA to a patient optionally in combination with a monokine and/or hyaluronidase.

It is a further object to provide a method of lowering the blood cholesterol level in a human patient comprising administering a cholesterol lowering amount of LTA to such human patient.

It is a further object to provide a method of producing the new LTA and the new pharmaceutical preparation.

It is a further object to provide two degradation products of the new LTA and their use.

It is a further object to provide a new Streptococcus strain from which the new LTA can be isolated and a method for its proliferation.

BRIEF DESCRIPTION OF THE DRAWING

For a better understanding of the invention, an exemplary embodiment is described below, considered together with the accompanying FIGURE, in which.

Figure 1:
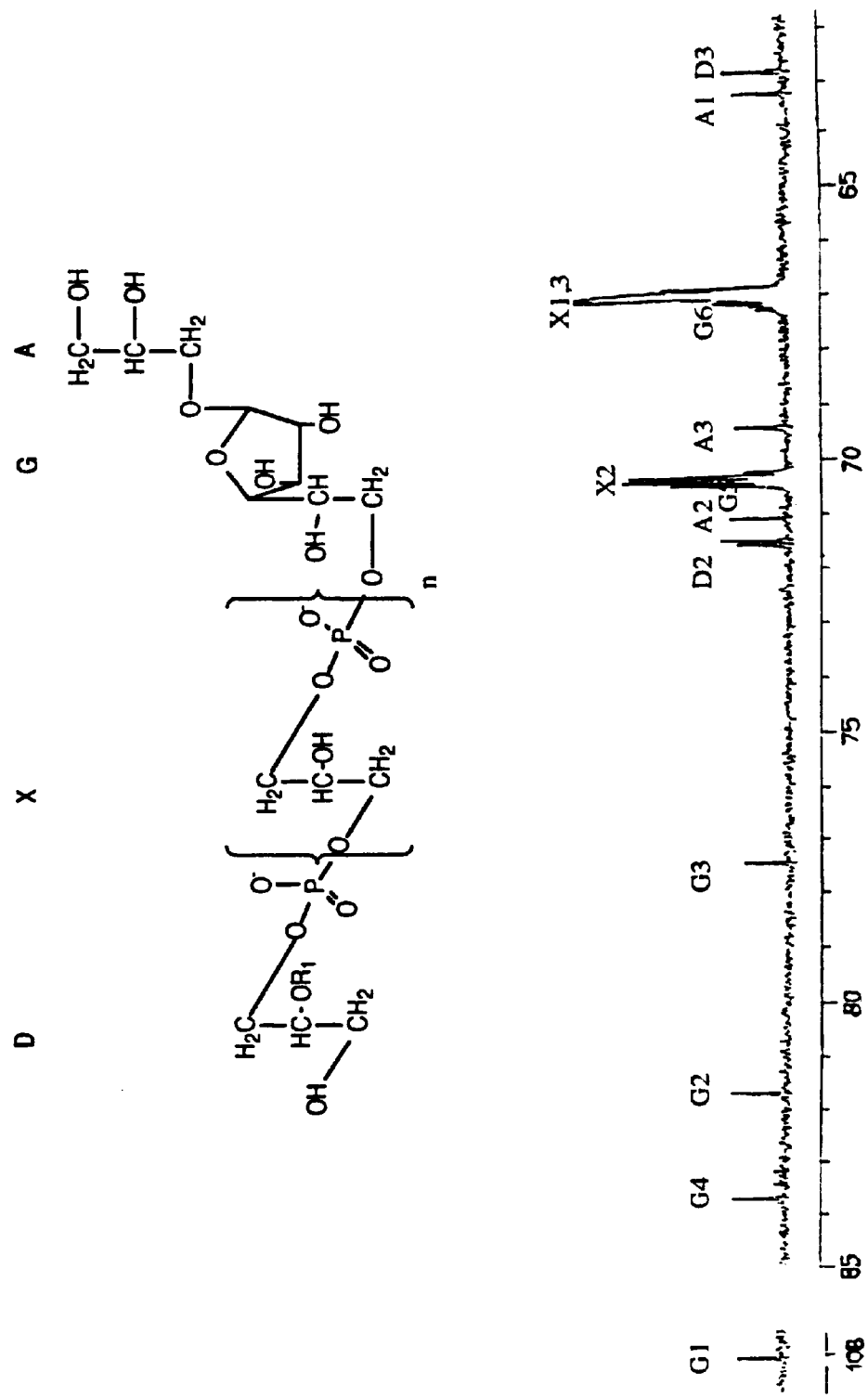
FIG. 1 shows the formula of a lipoteichoic acid (LTA-T) isolated from the Streptococcus sp strain DSM 8747 and the NMR spectrum of the deacylated compound of LTA-T.

It is to be understood that the drawing is to aid in understanding the concepts of the invention and is not limiting in nature.

DETAILED DESCRIPTION OF THE INVENTION

The invention concerns a new purified lipoteichoic acid (LTA) isolatable from the new Streptococcus sp strain DSM 8747.

A first new LTA found is designated as LTA-T. It consists of a defined compound as it is shown in Formula I, with a microheterogeneity of chain length and fatty acid composition as it is given in the table on page 3. This microheterogeneity is a typical feature of lipid macroamphiphiles [Fischer W. (1993), Molecular analysis of lipid macroamphiphiles by hydrophobic interaction chromatography, exemplified with lipoteichoic acids, Anal. Biochem., 208, 49–56]. The exact composition of the naturally occuring LTA-T cannot easily be determined. It depends on the conditions of cultivation of the microorganisms.

More particularly the invention provides a lipoteichoic acid LTA-T of the Formula I

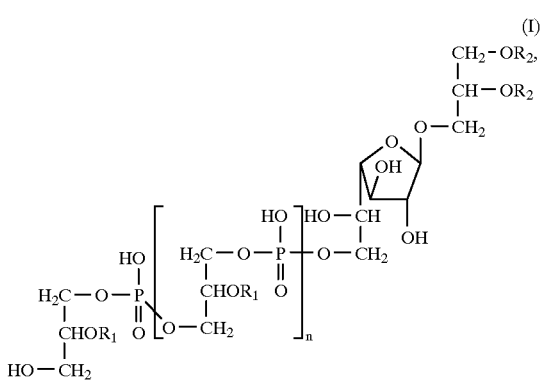
(I)

wherein $R_1$ is hydrogen or D-alanyl with a molar ratio to phosphorous of 0.27 to 0.35, and $R_2$ are the residues of saturated or unsaturated fatty acids with 12, 14, 16 or 18 carbon atoms and the mean value for n is 9, and salts thereof.

LTA-T is a new type of lipoteichoic acid in that it contains a monohexosylglycolipid moiety. Such monohexosylglycolipid moiety has not been found yet in other organisms as a part of lipoteichoic acids. This lipidanchor, as shown in Formula II below, is a beta-galactofuranosyl(1-3)glycerol-di-$R_2$-ester wherein $R_2$ are different rests of fatty acids esterified to the two adjacent hydroxy groups in the glycerol moiety.

The fatty acid rests $R_2$ are derived from straight-chain saturated or mono-unsaturated carboxylic acids having 12, 14, 16, or 18 carbon atoms and include the saturated lauric (C-12), myristic (C-14), palmitic (C-16) and stearic (C-18) acid, and corresponding mono-unsaturated carboxylic acids with one double bond in 7, 9, 11 or 13 position, respectively. The distribution is heterogenous and reflects the distribution in whole membrane lipids. Following aproximative percentages have been found for $R_2$ for a typical cultivation:
C-12, saturated: ca. 6.0%;
C-14, saturated: ca. 17.0%;
C-14, mono-unsaturated (position unknown) ca. 3.7%;
C-16, saturated: ca. 33.0%
C-16, mono-unsaturated probably in 7-position: ca. 3.8%;
C-16, mono-unsaturated in cis-9-position: ca. 11.3%;
C-16, mono-unsaturated in cis-11-position: ca. 2.4%;
C-18, saturated: ca. 10.0%
C-18, mono-unsaturated probably in 9-position: ca. 3.2%
C-18, mono-unsaturated in 11-position (cis): ca. 8.5%
C-18, mono-unsaturated probably in 13-position: ca. 1.1%.

The hydrophilic backbone consists of a poly (glycerophosphate) with a mean of 10 glycerophosphate units. The hydroxygroups at position 2 of the glycerol moieties are free or esterified by D-alanine. The molar ratio of substitution to phosphorous is 0.27–0.35, corresponding to 2.7 to 3.5 D-alanine groups per molecule LTA-T. The D-alanine content depends on the cultivation conditions.

The free hydroxy groups at the phosphorous atoms are acidic. At pH 4.7 in sodium acetate buffer and in physiological saline the cation is a sodium ion. LTA-T may form salts with other positively charged ions, in particular physiologically acceptable salts, such as alkali metal or alkaline earth metal salts, also heavy metal salts, such as zinc or iron salts, or primary, secondary, tertiary or quaternary ammonium salts (acid addition salts). Such other salts are e. g. potassium, calcium, ammonium, mono-, di-, tri- or tetra-lower alkyl-, e. g. methyl- or ethyl-, or methyl-ethyl, propyl- or butyl-ammonium salts. Non-physiologically acceptable salts, such as heavy metall salts, e. g. copper salts, may be used for isolation and purification of LTA-T. A preferred salt is the sodium salt, when the LTA is purified as described.

For therapeutical use the amount of the positively charged ions in the pharmaceutical composition is to be adjusted to result in a physiologically acceptable pH, in particular around pH 7 or 7.2.

The invention concerns a method for the preparation of a lipoteichoic acid LTA-T, characterized in isolating it from Streptococcus sp (DSM 8747) and purifying it by conventional methods.

Isolation and purification of LTA-T can be achieved in analogy to Fischer W., Koch H. U., Haas R. (1983), Improved preparation of lipoteichoic acids, Eur. J. Biochem., 133: 523–530, or any other method. For example, bacteria cells (DSM 8747) are suspended in distilled water or preferably a buffer, e. g. citrate buffer of pH 3.0, and disrupted, e. g. by means of a homogenizer and glas beads, preferably under cooling. The suspension of the broken cells is adjusted to about pH 4.7, e. g. with sodium bicarbonate. The aqueous suspension is extracted with phenol at moderately elevated temperature, e. g. up to about 68° C. The water phase is separated and several times dialysed, e. g. against sodium acetate buffer of pH 4.7, with a diaphragma having a molecular weight cut off of 10–12 kD. The remaining clear solution is concentrated in an ultrafiltration device with a PM 10 membrane and insoluble material, such as polysaccharides, removed by centrifugation.

The crude extract is further freed from undesired material, such as proteins, nucleic acids and polysaccharides, e. g. by hydrophobic interaction chromatography (HIC), e. g. by loading in a solution of propanol/sodiumacetate pH 4.7 on an octyl-Sepharose column. The LTA-T is eluted, e.g with a linear gradient of propanol in sodium acetate pH 4.7. The effluents are monitored by a colorimetric determination of organic phosphorus according to Schnitger H., Papenberg K., Ganse E., Czok R., Bücher T., Adam H. (1959), Chromatographie phosphathaltiger Metabolite eines menschlichen Leberpunktats, Biochem. Zentralblatt, 332: 167187. LTA-T is eluted at a propanol concentration of about 30–38%. The LTA-T containing fractions are dialysed against a buffer, e. g. sodiumacetate pH 4.7, and concentrated by ultrafiltration with a PM 10 membrane or completely dried in vacuum. The purified LTA-T or the concentrated solution thereof is stored at −20° C.

The bacteria cells (DSM 8747) are obtained by culturing in a conventional manner in a complex medium, e. g. Todd Hewitt broth or Tryptic Soy broth, at 37° C. and a pH of about 7.2 under stirring and without aeration. At the end of the logarithmic growth phase the cells are harvested, e. g. by centrifugation, suspended in a convenient buffer, e. g. a citrate buffer of pH 3, in which they can be stored at low temperature, e. g. at −20° C. for further use.

The invention concerns further a pharmaceutical preparation comprising a lipoteichoic acid LTA-T or a physiologically acceptable salt thereof, optionally in combination with a monokine and/or hyaluronidase.

Monokines are for example interferons, such as of the alpha group, e. g. interferon alpha 2b, or interferon gamma, cytokines, are for example inter-leukins, e. g. interleukin-1-alpha, -1-beta, -1-ra, -2, -3, -4, -5, -6 -7 or -8, tumor-nekrose-factors, e. g. TNF-alpha or -beta, or TGF-beta-1, -beta-2, -beta-3, -beta-5 and -alpha.

Hyaluronidase is any commercially available one, e.g. PERME ASE®.

The pharmaceutical preparations are of conventional manner.

The LTA-T or the pharmaceutical combinations of the present invention are administered orally or parenterally to achieve the therapeutic effect in any of the usual pharmaceutical forms. These include solid and liquid unit oral dosage forms such as tablets, capsules, powders, suspensions, solutions and syrups, transdermal plasters, inhalable formulations, and the like, including sustained release preparations, and fluid injectable forms, such as sterile solutions and suspensions. The term dosage form as used in this specification and the claims refer to physically discrete units to be administered in single or multiple dosage to humans or warmblooded animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitably fine size and mixing with a similarly comminuted diluent pharmaceutical carrier, such as an edible carbohydrate material as for example, starch. Sweetening, flavoring, preservative, dispersing and coloring agents can also be added. Powders are advantageously applied by inhaling and are for this purpose filled into inhalers. Such inhalers for dry powders are known in the art.

Capsules are made by preparing a powder as described above and filling formed gelatin sheaths. A lubricant, such as talc, magnesium stearate and calcium stearate can be added to the powder mixture as an adjuvant before the filling operation. A glidant such as colloidal silica may be added to improve flow properties. A disintegrating or solubilizing agent may be added to improve the availability of the medicament when the capsule is ingested.

Tablets are made by preparing a powder mixture, granulating or slugging, adding a lubricant and disintegrant and pressing into the desired form. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then pressed into tablets. The medicaments can also be combined with free flowing inert carriers and compressed into tablets directly without going through the granulating or slugging steps. A protective coating consisting of a sealing coat of shellac, a coating of sugar or polymeric material and polish coating of wax can be provided. The coating can be resistant in the stomach and the active ingredients to be released in the intestine. Dyestuffs can be added to these coatings to distinguish different unit dosages.

Oral fluids such as syrups and elixirs can be prepared in unit dosage form so that a given quantitiy, e.g. a teaspoonful, contains a predetermined amount of the compound. Syrups can be prepared by dissolving the active compound in a suitably flavored aqueous sucrose solution, while elixirs are prepared through the use of a non-toxic alcoholic, e.g. ethanolic, vehicle. Suspensions and emulsions can be formulated by dispersing the medicament in a non-toxic vehicle.

For parenteral administration, fluid unit dosage forms can be prepared by suspending or dissolving a measured amount of the active material in a non-toxic liquid vehicle suitable for injection such as an aqueous, alcoholic, e. g. ethanolic, or oleaginous medium. Such fluid dosage unit forms may contain solubilizers, such as a polyethyleneglycol, stabilizers, and buffers, such as a citric acid/sodium citrate buffer, to provide the desired osmotic pressure. Alternatively a measured amount of the active material is placed in a vial and the vial and its contents are sterilized and sealed. An accompanying vial or vehicle can be provided for mixing prior to administration. Solutions can also be specifically prepared for inhalation and applied by means of an inhaler. Inhalers for fluids are known in the art.

For transdermal application powders or syrups may be manufactured into suitable transdermal plasters. Such plasters are known in the art.

If combinations of LTA-T with a monokine and/or hyaluronidase are envisaged such combinations may be used separately and simultaneously or consecutively, or otherwise formulated together in one pharmaceutical preparation according to the methods described above.

The invention concerns further a method of producing a pharmaceutical preparation comprising LTA-T or a physiologically acceptable salt thereof and optionally a monokine and/or hyaluronidase by a conventional method.

The invention concerns further a method of treating cancer comprising administration of an antitumor effective amount of a lipoteichoic acid LTA-T or a physiologically acceptable salt thereof and optionally a monokine and/or hyaluronidase to a patient suffering from cancer, a tumor or a malignant cell thereof.

The following biological effects, determined according to Bhakdi S., Klonisch T., Nuber P., Fischer W., Stimulation of monokine production by lipoteichoic acids, Infect. Immun., 59(12): 4614–4620, (1991), and Keller R., Fischer W., Keist R., Bassetti S., Macrophage response to bacteria: induction of marked secretory and cellular activities by lipoteichoic acids, Infect. Immun., 60(9): 3664–3672, (1992), respectively, were found 8 hours after induction of monocytes with LTA-T:

TABLE 1

| Amount of LTA-T used for Induction, ug | Amount of monocytes found 8 h after induction, ng ml$^{-1}$ |
|---|---|
| 0.50 | TNF: 25 |
| 1.50 | TNF: 60 |
| 0.25 | IL-6: 27 |
| 2.00 | IL-6: 30 |
| 1.00 | IL-1b: 35 |
| 4.00 | IL-1b: 35 |

The values for induction with the known LTAs of *S. pyogenes* and *S. lactis* as obtained in the same set of experiments were 2–4 times less than these data.

The new LTA-T is preferably administered subcutaneously, intravenoulsy or intraperitoneally in dosage unit form of a pharmaceutical preparation comprising LTA-T or a physiologically acceptable salt thereof in an amount of from 0.1 to 20 micromol/ml and one or more pharmaceutical carriers. An antitumor effective amount of LTA-T is e. g. of from about 0.001 to about 20 mg, e. g. from 1 to 20 mg/kg, preferably of from 0.01 to 2 mg/kg, which is administered to a patient of normal weight once or preferably several times during the entire period of treatment, as need may be. The amount and mode of administration depend on the type and severity of the disease, the weight and general condition of the patient and is to be left to the judgement of the physician. The new LTA-T may be applied prophylactically in the amounts given hereinbefore.

If hyaluronidase is used it is applied in amounts of between about 500 and about 5000, preferably about 1000 U USP, and preferably subcutaneously.

If a monokine is used it is applied in amounts of between about 0.1×10⁶ and about 20×10⁶, preferably about 6×5 mio units, and preferably subcutaneously.

Eight patients suffering from various kinds of tumors/cancer were treated subcutaneously with a solution having a concentration of 1 micromol/ml LTA-T in physiological saline in single or repeated administration. Most of the patients obtained also subcutaneously hyaluronidase and one obtained also an interferon-alpha. The results are compiled in Example 7, Table 2.

The invention concerns further the new. Streptococcus sp strain DSM 8747 from which the new LTA-T can be isolated.

The new bacteria strain was isolated from an erysipelas of a female patient with a malignant breast carcinoma in complete remission. The strain is a new species within the genus streptococcus. It was designated as Streptococcus sp. PT and deposited under the Budapest Treaty at the Deutsche Sammlung für Mikroorganismen, Braunschweig, Germany, under the deposition number DSM 8747 on Nov. 25, 1993.

The strain can be cultured and stored under conventional conditions as described hereinbefore.

The invention concerns further the new degradation products of LTA-T and the methods of their preparation by conventional means, e. g. by alkaline or hydrogen fluoride (HF) hydrolysis.

Such new degradation product is for example the deacylated dLTA-T of the Formula I, wherein $R^1$ and $R^2$ are both hydrogen. This compound is obtained by splitting off the fatty acid and the D-alanyl groups by conventional methods, e. g. by treatment of LTA-T with a base, e. g. 0.1 m aqueous NaOH at 37° C. for about one hour. The formed dLTA-T is separated and purified according to the method of Folch J, Lees M., Sloan-Stanley, G. M. S. (1957), a simple method for the isolation and purification of total lipids from animal tissues, J. Biol. Chem. 226, 497–509, by partition between the two phase system chloroform:methanol:water (1:0.9:0.9).

Another new degradation product is beta-galactofuranosyl(1-3)glycerol-di-$R_2$-ester of the Formula II

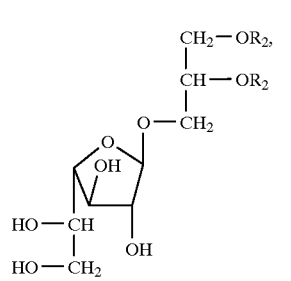

(II)

wherein $R_2$ is the rest of a saturated or unsaturated fatty acid with 12, 14, 16 or 18 carbon atoms, a single compound falling under Formula II, and salts thereof.

A compound of the Formula II is produced from a compound of the Formula I by splitting the bond between the 6-hydroxy group of the galactofuranosyl group and the phosphoric acid moiety, e. g. by treatment of LTA-T with 48% hydrogen fluoride at 2° C. for about 36 hours.

A compound of the formula II, wherein $R_2$ is hydrogen (deacylated lipid anchor) is produced from a compound of the formula I, e. g. by treatment with 0.2 M NaOH for 12 hours at 100° C., and subsequent cleavage of phosphomonoesters by phosphomonoesterase.

The degradation products are useful as analytical tools for the identification and characterization of LTA-T and as starting materials for the preparation of new LTAs with defined groups $R^2$, for example by esterification of dLTA-T with specific fatty acids, and for the preparation of new LTA with a defined hydrophilic group esterified to the 6-hydroxy group of the galactofuranosyl moiety.

The following examples describe the invention in more detail. They should however not be construed as a limitation thereof.

EXAMPLE 1

Bacterial Strain and Cultivation

The gram-positive bacterium Streptococcus sp. PT, deposited at the Deutsche Sammlung für Mikroorganismen unter No. DSM 8747, was isolated from a erysipelas of a human patient with a malignant breast carcinoma. It belongs to the group of streptococci. 16 S RNA sequencing revealed that this strain cannot be classified in the known groups of streptococci. It was designated Streptococcus sp PT and has the following growth characteristics:

Morphology: chain forming cocci with 5–40 units, depending on shear forces

Growth optima: $pH_{opt}$: pH 7.2; $T_{opt}$: 37° C.; microaerophilic growth

The bacteria are cultivated in Todd Hewitt broth (Difco, USA) to the end of the logarithmic growth phase. Cultivation conditions are:

Working Volume $V_R$: 500 l

Temperature: 37° C.

pH: 7.2±0.1

Aeration rate: none–0.05 vvm

Stirring speed: 500 rpm

The culture broth is cooled and the cells harvested immediately by centrifugation. The cells (400 g wet weight per liter) are suspended in 0.1M citrate buffer pH 3.0 and stored at −20° C. for further use.

EXAMPLE 2

Isolation and Purification of Lipoteichoic Acid LTA-T

When not mentioned otherwise all steps are accomplished at 4° C.

A suspension (250 ml) of bacteria cells DSM 8747 in 0.1 M citrate buffer pH 3.0 (400 g wet weight per liter, obtained as described in Example 1) is mixed with an equal volume of glass beads (Braun Melsungen, Ø 0.17–0.18 mm) and agitated under cooling in a Braun disintegrator fitted with a $CO_2$ cooling device for 6 min. The suspension of broken cells is decanted through a glass filter G1 and the remaining glass beads are washed with 0.1 M of sodium acetate pH 4.7. The combined filtrate and washing fluid is adjusted to pH 4.7 with 1 M $NaHCO_3$. The crude suspension is extracted in an equal volume of 80:20 (v/v) phenol/water at 68° C. for 1 hour. After cooling, the water phase is separated by centrifugation at 3000 rpm (1800 g) for 30 minutes. The upper water phase is collected and an equal volume of 0.1 M sodiumacetate buffer pH 4.7 is added to the remaining phenol phase and extracted, centrifuged and collected as described before. If the water phase is cloudy, it is extracted again with phenol at room temperature (⅛ (v/v) of the water volume) for 30 min and centrifuged as before.

The combined water phases are extensively dialysed against 0.05 M sodiumacetate pH 4.7 (four 5 liter changes for at least 24 h) in a Medicell® tubing with a molecular weight cut off (MWCO) of 10–12 kD.

The clear solution is concentrated in an Amicon® Ultrafiltration device with a PM 10 membrane (MWCO 10 kDa) and insoluble material (e. g. polysaccharides) is separated by centrifugation.

The crude extract solution is freed from proteins, nucleic acids and polysaccharides by hydrophobic interaction chromatography (HIC). For that purpose the crude LTA preparation is loaded in 15% propanol in 0.1 M sodiumacetate pH 4.7 on an octyl-Sepharose (Pharmacia LKB Sweden) column, previously equilibrated with the same buffer-propanol solution. After separation of nucleic acids, proteins and polysaccharides, the LTA-T is eluted with a linear gradient of 15–55% (v/v) propanol in 0.1 M sodiumacetate pH 4.7. Each effluent is monitored by a colorimetric determination of organic phosphorus according to Schnitger, ibid. The LTA is eluted at a propanol concentration of about 33%. The LTA containing fractions are collected and dialysed against 0.05 M sodiumacetate pH 4.7 and concentrated down to about 5 micromol phosphorus content/ml by ultrafiltration in an Amicon® Ultrafiltration device with a PM 10 membrane (MWCO 10 kDa). The concentrated solution of LTA-T is stored at −20° C.

This clear solution of LTA-T is free of contaminant proteins (shown by HPLC of amino acids after acid hydrolysis), nucleic acids (exact Gro/P ratio) and carbohydrates (no contaminant sugars after acid hydrolysis). It can be evaporated to dryness to give a powder which is difficult to solubilize again in water for reason of micell formation. It can be solubilized in a mixture of water and an organic solvent, e. g. ethanol, or a solubilizer, e. g. polyethyleneglycol.

The LTA-T can be characterized by its unique lipidanchor after hydrolysis with hydrogen fluoride, as described in Example 3.

EXAMPLE 3

Structural Characterization

The purified LTA is submitted to HF hydrolysis (48% HF, 36 h, 2° C.) and the hydrophilic part (products of the backbone) and the hydrophobic part (lipidanchor) separated by Folch partition [Folch J., Lees M., Sloane-Stanley G. H. S. (1957), a simple method for the isolation and purification of total lipids from animal tissues, J. Biol. Chem., 226: 497–509] in chloroform:methanol:water (1:0.9:0.9).

The two parts are analyzed separately. The core of the lipid anchor is analysed after deacylation as partially methylated alditol acetate by GLC-MS analysis. The typical fragmentation pattern of 1,2-dimethyl-3-acetyl-glycerol and 2,3,5,6-tetra-0-methyl-1,4-di-0-acetyl-galactitol can be observed. The hydrophilic products are analyzed by GLC (gas liquid chromatography) before and after HCl hydrolysis or alkaline dealanylation. Thereby no sugars are detected.

For molecular composition the LTA is hydrolysed with 2M HCl for 2.5 hours at 100° C. and afterwards treated with phosphonomonoesterase in order to remove phosphonomonoesters. Phosphorus, glycerol, galactose and alanine are obtained in a ratio of 1:1.05:0.11:0.27 indicating the proposed structure given by Formula I. [According to the methods described in Fischer W. (1988), Physiology of lipoteichoic acids in bacteria, Adv. Microb. Physiol., 29 (233): 233–302].

NMR analysis of the deacylated compound of LTA-T (dLTA-T) allows a definite structural characterization. The NMR spectrum is shown in FIG. 1. The identification of the peaks are listed in the following Table 2:

TABLE 2

| C-atom | dLTA | | ppm | | ppm |
|---|---|---|---|---|---|
| beta-G1 | 108.24 | Gro A1 | 63.45 | X1 | 67.14 |
| G2 | 81.83 | A2 | 71.16 | X2 | 70.40 |
| G3 | 77.61 | A3 | 69.50 | X3 | 67.00 |
| G4 | 83.82 | D1 | 67.37 | | |
| G5 | 70.50 | D2 | 71.62 | | |
| G6 | 67.27 | D3 | 63.04 | | |

Summing up, the characteristics of this LTA for distinction of other LTAS are the following:
- beta-Galf-(1-3)diacylglycerol as lipid anchor
- non-glycosylated, linear, unbranched GroP-chain
- mean chain length of 10 GroP units
- lipid pattern

EXAMPLE 4

Preparation of Deacyl-LTA-T (dLTA-T)

LTA-T is submitted to mild alcaline hydrolysis (0.1M NaOH, 1 h, 37° C.). The solution is adjusted to pH 3 with HCl and the fatty acids are extracted four times with petroleum-ether:chloroform (4:1). The water solution is neutralized with NaOH and extensively dialysed against water in a tubing with a cut off of 2 kD. The product in the retentate is LTA-T without alanine esters and without fatty acids and is called dLTA-T.

EXAMPLE 5

Preparation of beta-Galactofuranosyl(1-3)glycerol-di-$R_2$-ester

The lipidanchor beta-galactofuranosyl(1-3)glycerol-di-$R_2$-ester of the Formula II can be isolated as it is outlined in Example 3 after HF hydrolysis.

Since galactofuranosyl-beta-1-3-glycerol is also found as a part of the membrane lipids, it can be isolated from whole lipid preparations.

The lipids are isolated by the method of Bligh-Dyer [Bligh E. G., Dyer W. J. (1959, a rapid method of total lipid extraction and purification, Can J. Biochem Physiol, 37: 9111–9117] and the crude lipid extract is first fractionated on an anion exchange column (DEAE Cellulose) and further purified on silicagel. Elution is made with different mixtures of chloroform:acetone. Final purification is made by preparative TLC on silicagel plates [Kates M. (1986) Techniques in lipidology. In: Laboratory techniques in biochemistry and molecular biology. Work T. S., Work E. (eds.), North-Holland publishing company, Amsterdam].

EXAMPLE 6

Pharmaceutical Formulation

The purified LTA-T in 0.05M sodiumacetate pH 4.7 is dialysed extensively against physiological NaCl solution (0.9%) and the volume is adjusted to 1 μmol LTA-T (based on the phosphorus content) with physiological saline. After filtration of the solution through a filter membrane (Millipore 0.22um), 1 ml aliquots of the filtrate are placed in sterilized vials under sterile conditions. These vials contain 1 micromol/ml LTA-T phosphorus and are used subcutaneously for therapeutical purposes.

EXAMPLE 7

Results of Clinical Treatments

Eight patients suffering from various kinds of tumors/cancer were treated subcutaneously with a solution having a concentration of 1 micromol/ml LTA-T in physiological saline in single or repeated administration. Most of the patients obtained also subcutaneously hyaluronidase and one obtained also an interferon-alpha. The results are compiled in Table 3:

TABLE 3

| Patient | Type of Tumor | Treatment | Result |
|---|---|---|---|
| M.F., *1952 | Malignant fibrous Histiocytoma. Removed surgically 3/91. Local recurrence 5/92. Incomplete excision 11/92. | LTA-T s.c. at the site of the tumor. Total dose 8 micromol phosphate[1]: 1-2/93 | CR (>10 months) |
| H.R., *1909 | Cancer of the Prostate, diagnosed 6/92 | 7/92: LTA-T, 1 micromol P in combination with Hyaluronidase[2] 1000 NFU s.c. 9/93: LTA-T, 2 micromol P incombination with Hyaluronidase 1000 NFU s.c. | PR (PSA: 6/92: 108 mcg/1, 9/92: 63 mcg/1) |
| L.B., *1943 | Colon carcinoma pT3 pN2 G2, Resection 1/90 | LTA-T 3/90: 8 micromol P in combination with Hyaluronidase 1000 NFU s.c. 3/91: 8 micromol P in combination with Hyaluronidase 1000 NFU s.c., 12/91: 8.micromol P in combination with Hyaluronidase 1000 NFU s.c., 11/92: 3 micromol P in combination with Hyaluronidase 1000 NFU s.c., 9/93: 3 micromol P in combination with Hyaluronidase 1000 NFU s.c. | CR (>47 months) |
| L.K., *1916 | Colon carcinoma pT4 pN2 G2-3, Resection 4/93 | LTA-T 5/93: 6 micromol P in combination with Hyaluronidase 1000 NFU s.c. | CR (>6 months) |
| M.R., *1941 | Breast carcinoma 3/90: Lumpectomy 6/92: Recurrence: in regional Lymphnodes and Lung | LTA-T 10/93: 3 micromol P in combination with Hyaluronidase 1000 NFU and Interferon alpha 2b[3], 5 mio U, 6 times s.c. | PR |
| F.M., *1913 | Lung carcinoma 2/91: Adenocarcinoma right upper lobe | LTA-T 9/92: 2 micromol P in combination with Hyaluronidase 1000 NFU s.c. | PR (>14 months) |
| A.L., *1922 | Inflammatory breast carcinoma with bone metastasis 2/92 | LTA-T 7/92: 9 micromol P in combination with Hyaluronidase 1000 NFU s.c. | Primary tumor: CR 14 months Bone metastasis: PD (died 9/93) |
| C.H., *1921 | Breast carcinoma with lung and mediastinal metastasis | LTA-T 7/92: 2 micromol P in combination with Hyaluronidase 1000 NFU s.c. | PR of mediastinal mass |

[1] the dosage is calculated on the amount of phosphate of the LTA-T preparation
[2] the hyaluronidase was obtained from CILAG as PERMEASE ®
[3] the interferon-alpha 2b was obtained from ESSEX CHEMIE as INTRON H ®
Abreviations: CR: complete remission; PR: partial remission;*: birth year; PSA: prostate specific antigen; U USP: units United States Pharmacopoe; P; phosphate content;

Deposit of Microorganism:

The microorganism PT designated as Streptococcus sp PT, used in this invention was deposited under the Budapest Treaty on Nov. 25, 1993, under the number DSM 8747 at the DSM-DEUTSCHE SAMMLUNG VON MIKROORGANISMEN UND ZELLKULTUREN GmbH, Mascheroder Weg 1b, D-38124 Braunschweig.

We claim:

1. Isolated Streptococcus sp PT strain DSM 8747.

2. A method for the proliferation of Streptococcus sp PT strain DSM 8747 wherein said method comprises growing said strain under proliferating conditions.

3. The method of claim 2 in which said proliferating conditions comprise culturing said strain in a complex medium at a temperature of about 37° C. and pH of about 7.1 to 7.3.

* * * * *